(12) United States Patent
Inada et al.

(10) Patent No.: US 12,734,163 B2
(45) Date of Patent: Sep. 15, 2026

(54) PHARMACEUTICAL PREPARATION AND METHOD FOR PRODUCING THE SAME

(71) Applicants: Fuji Pharma Co., Ltd., Tokyo (JP); KinoPharma, Inc., Tokyo (JP)

(72) Inventors: Toshiyuki Inada, Toyama (JP); Takaki Shimodaira, Toyama (JP); Ryosei Kanayama, Toyama (JP); Hiroshi Onogi, Tokyo (JP); Tetsuo Yamaguchi, Tokyo (JP)

(73) Assignees: Fuji Pharma Co., Ltd., Tokyo (JP); KinoPharma, Inc., Tokyo (JP)

( * ) Notice: Subject to any disclaimer, the term of this patent is extended or adjusted under 35 U.S.C. 154(b) by 645 days.

(21) Appl. No.: 17/605,747

(22) PCT Filed: Apr. 24, 2020

(86) PCT No.: PCT/JP2020/017711
§ 371 (c)(1),
(2) Date: Oct. 22, 2021

(87) PCT Pub. No.: WO2020/218518
PCT Pub. Date: Oct. 29, 2020

(65) Prior Publication Data

US 2022/0211688 A1 Jul. 7, 2022

(30) Foreign Application Priority Data

Apr. 25, 2019 (JP) ................................ 2019-084695

(51) Int. Cl.
*A61K 31/4545* (2006.01)
*A61K 9/48* (2006.01)
*A61K 9/50* (2006.01)

(52) U.S. Cl.
CPC ........ *A61K 31/4545* (2013.01); *A61K 9/4866* (2013.01); *A61K 9/5089* (2013.01)

(58) Field of Classification Search
CPC .............. A61K 31/4545; A61K 9/4866; A61K 9/5089; A61K 9/2018; A61K 9/2054; A61K 9/2059; A61K 9/2081; A61K 9/5078; A61K 9/1652; A61K 9/1623; A61K 9/5036; A61K 47/38; A61P 31/12; A61P 43/00
See application file for complete search history.

(56) References Cited

U.S. PATENT DOCUMENTS 6,638,530 B1 10/2003 Ishibashi et al.
2011/0092598 A1* 4/2011 Deorkar ............... A61K 31/192
514/629

FOREIGN PATENT DOCUMENTS

CN 1473054 A 2/2004
JP 2003-508386 A 3/2003
JP 2006-016329 A 1/2006
JP 2007-517062 A 6/2007
JP 2015-48315 A 3/2015
JP 2015048315 A * 3/2015
WO 2005/065647 A2 7/2005
WO WO-2009020198 A1 * 2/2009 ............. A61P 31/12
WO WO-2010038688 A1 * 4/2010 ............ A61K 31/40
WO 2010/095494 A1 8/2010

OTHER PUBLICATIONS

JP 2015048315 A1 Translated (Year: 2015).*
WO 2009020198 A1 translated (Year: 2009).*
WO 2010038688 A1 translated (Year: 2010).*
(Continued)

*Primary Examiner* — Robert A Wax
*Assistant Examiner* — John Seungjai Kwon
(74) *Attorney, Agent, or Firm* — Sughrue Mion, PLLC

(57) ABSTRACT

Disclosed is a pharmaceutical preparation in the form of granules having nuclear particles and a coating layer coating the nuclear particles, wherein the nuclear particles are composed of a drug, a first nuclear-particle component, a second nuclear-particle component and a surfactant; the drug is an aniline derivative represented by the following general formula (I):

[Formula 1]

(I)

wherein W represents S or O, or a pharmaceutically acceptable salt thereof, or a hydrate thereof; the first nuclear-particle component is at least one crystalline cellulose having a shape selected from a needle-shape and a substantially columnar shape; and the second nuclear-particle component is at least one pharmaceutically acceptable additive having a substantially spherical shape. The pharmaceutical preparation can contain a therapeutically effective amount of a poorly water-soluble drug (CDK9 inhibitor) and has excellent flowability sufficient for practical production.

40 Claims, 2 Drawing Sheets

(56) References Cited

OTHER PUBLICATIONS

Farber et al. (Microstructure of microcrystalline cellulose based granules prodced by high-shear wet granulation with long wet-massing time, Chemical Engineering Research and Design, 2018 (Year: 2018).*

Taiwanese Office Action dated Mar. 23, 2023 in Taiwanese Application No. 109113838.

Communication, dated Oct. 28, 2021, issued by the International Bureau in Application No. PCT/JP2020/017711.

Ajiro et al., "CDK9 Inhibitor FIT-039 Suppresses Viral Oncogenes E6 and E7 and Has a Therapeutic Effect on HPV-Induced Neoplasia", Clin Cancer Res., vol. 24, No. 18, pp. 4518-4528, Sep. 15, 2018, doi: 10.1158/1078-0432. CCR-17-3119. Epub Apr. 30, 2018 (11 pages total).

Tanaka et al., "Inhibitory effect of CDK9 inhibitor FIT-039 on hepatitis B virus propagation", Antiviral Res., vol. 133, pp. 156-164, 2016, doi: 10.1016/j.antiviral.2016.08.008. Epub Aug. 8, 2016 (9 pages total).

Okamoto et al., "Selective inhibition of HIV-1 replication by the CDK9 inhibitor FIT-039", Antiviral Res., vol. 123, pp. 1-4, 2015, doi: 10.1016/j.antiviral.2015.08.012. Epub Aug. 21, 2015 (4 pages total).

Yamamoto et al., "CDK9 inhibitor FIT-039 prevents replication of multiple DNA viruses", J Clin Invest., vol. 124, No. 8, pp. 3479-3488, 2014, doi: 10. 1172/JCI73805. Epub Jul 8, 2014 (11 pages total).

Office Action dated Nov. 3, 2022 from the China National Intellectual Property Administration in CN Application No. 202080030978.6.

International Search Report dated Aug. 4, 2020 from the International Searching Authority in International Application No. PCT/JP2020/017711.

* cited by examiner

[Figure 1A]
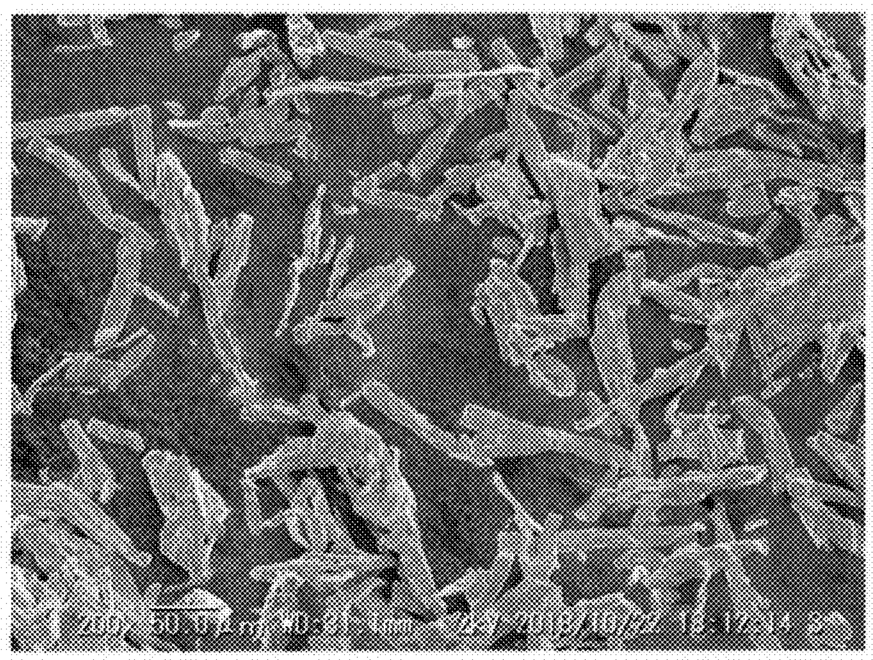
[Figure 1B]
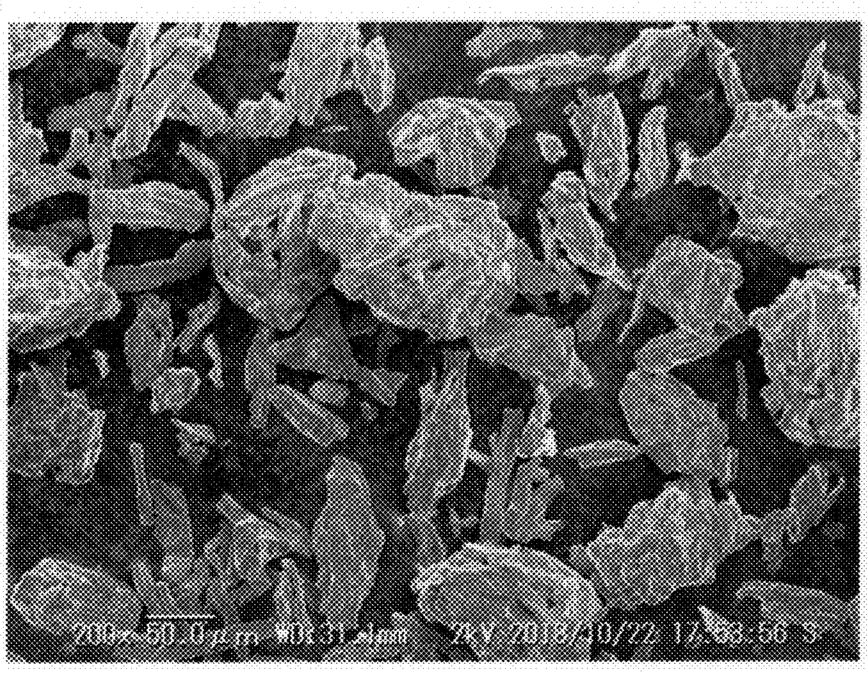

[Figure 2]
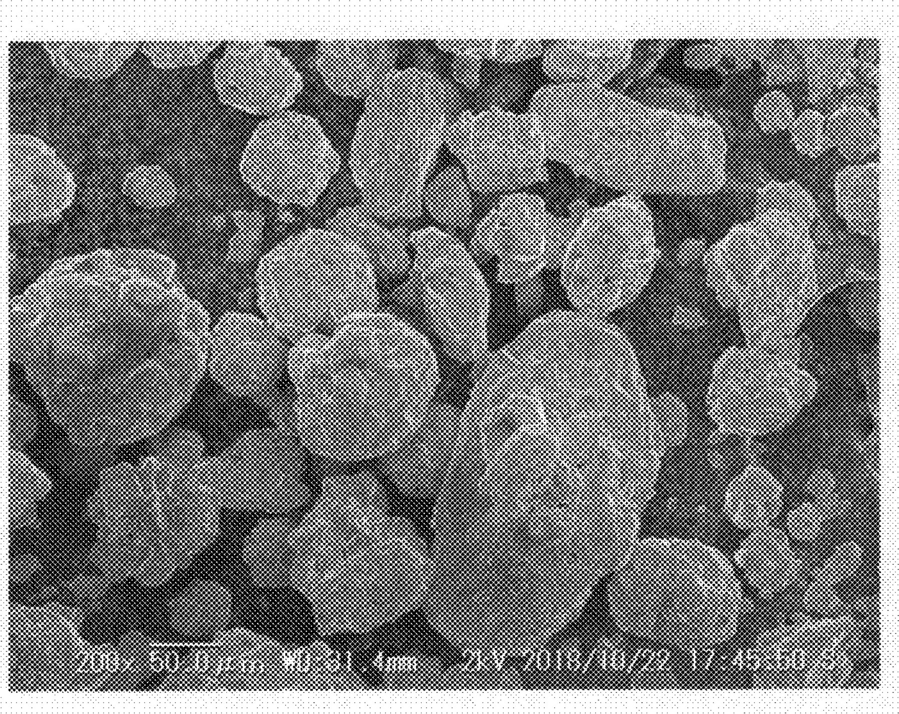
[Figure 3]
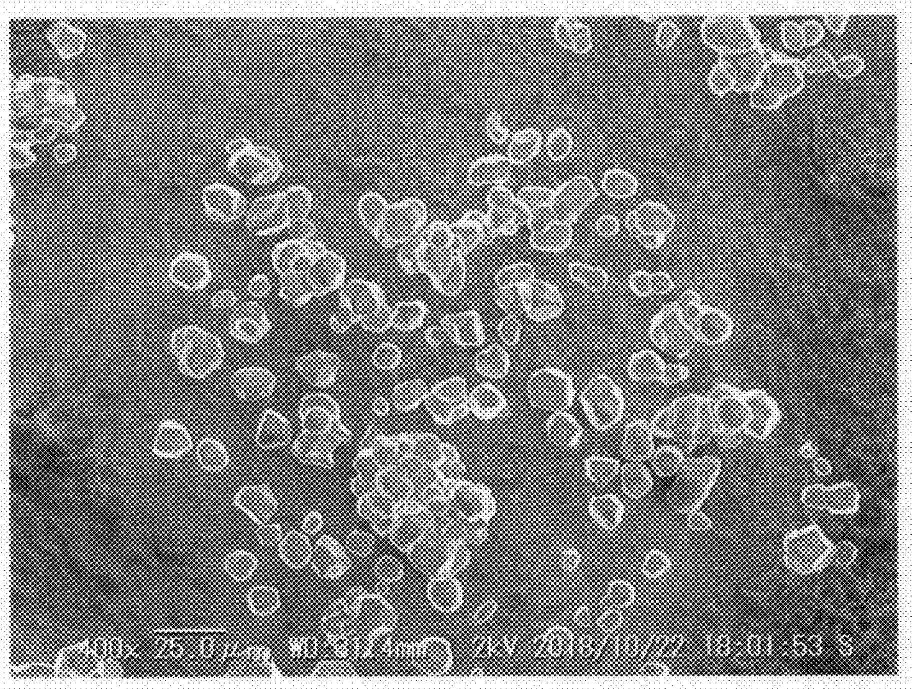

PHARMACEUTICAL PREPARATION AND METHOD FOR PRODUCING THE SAME

CROSS REFERENCE TO RELATED APPLICATIONS

This application is a National Stage of International Application No. PCT/JP2020/017711 filed Apr. 24, 2020, claiming priority based on Japanese Patent Application No. 2019-084695 filed Apr. 25, 2019.

TECHNICAL FIELD

The patent application contains a priority claim based on Japanese Patent Application No. 2019-84695 (filing date: Apr. 25, 2019), which was previously filed in Japan and the contents of which are incorporated herein in their entirety by reference.

The present invention relates to a pharmaceutical preparation and a method for producing the same.

BACKGROUND ART

It is known that an aniline derivative such as N-[5-fluoro-2-(1-piperidinyl)phenyl]isonicotinethioamide serving as a CDK9 inhibitor can be used as an antiviral drug for suppressing viral production (for example, (Non-Patent Documents 1 to 4).

However, some CDK9 inhibitors have low solubility to water. Due to this, it is difficult for them contained in preparations to dissolve in water in an effective amount and produce a sufficient medicinal effect.

Generally, as a solid preparation that can contain a poorly water-soluble drug in a therapeutically effective amount, soft capsules are widely used (for example, Patent Document 1). However, soft capsules are often large in size compared to other solid preparations such as tablets. Because of this, soft capsules have a problem in that it is difficult to take for small children/aged persons having poor ability to swallow and patients deteriorated in ability to swallow. Furthermore, soft capsules have an inherent risk of "easily leaking" although the risk varies depending on the production method. Moreover, soft capsules are flexible and easily change shapes. Due to this, the presence or absence of deformation of capsules must be visually inspected by a person or examined by a specialized inspection machine, with the result that production cost increases. High cost compared to other solid preparations such as tablets is a problem.

In contrast, in blending a poorly water-soluble drug in tablets, the poorly water-soluble drug is dissolved in a solvent before tableting. However, it is difficult to dissolve an effective amount of the poorly water-soluble drug in a solvent contained in a volume acceptable for preparing tablets.

It is known that granules composed of a drug and a solubilizing substance in combination are contained in pharmaceutical preparations. It is also known that a surfactant can be used as the solubilizing substance, and that granules can be coated (for example, Patent Document 2). However, a surfactant has adhesiveness/tackiness and reduces flowability. The surfactant for use in producing a pharmaceutical preparation such as tablets has a problem in that the content thereof is limited.

As described above, if a solubilizing substance such as a surfactant is used for adding a large amount of a poorly water-soluble drug such as a CDK9 inhibitor to a pharmaceutical preparation, sufficient flowability cannot be obtained during production of dosage form. Since low flowability affects formation of e.g., tablets, it is difficult to blend a therapeutically effective amount of a drug when dosage form such as tablets is formed.

CITATION LIST

Patent Documents

Patent Document 1: National Publication of International Patent Application No. 2003-508386

Patent Document 2: National Publication of International Patent Application No. 2007-517062

Non-Patent Documents

Non-Patent Document 1: Ajiro et. al., Clin Cancer Res. 2018 Sep. 15; 24(18):4518-4528. doi: 10.1158/1078-0432. CCR-17-3119. Epub 2018 Apr. 30

Non-Patent Document 2: Tanaka et. al., Antiviral Res. 2016 September; 133:156-64. doi: 10.1016/j.antiviral.2016.08.008. Epub 2016 Aug. 8

Non-Patent Document 3: Okamoto et. al., Antiviral Res. 2015 November; 123:1-4. doi: 10.1016/j.antiviral.2015.08.012. Epub 2015 Aug. 21

Non-Patent Document 4: Yamamoto et. al., J Clin Invest. 2014 August; 124(8):3479-88. doi: 10.1172/JCI73805. Epub 2014 Jul. 8

SUMMARY OF INVENTION

In view of the circumstances, it has been desired to develop a pharmaceutical preparation containing a therapeutically effective amount of a CDK9 inhibitor and having excellent flowability sufficient for practical production.

The present inventors conducted intensive studies and prepared a pharmaceutical preparation, which has nuclear particles containing a nuclear-particle component having a predetermined shape and a drug (CDK9 inhibitor) in combination, and a coating layer coating the nuclear particles. As a result, they found that the pharmaceutical preparation can contain a surfactant and the drug in large amounts and has excellent flowability. The present invention was made based on the findings.

The present invention includes the following inventions.

[1] A pharmaceutical preparation in the form of granules having nuclear particles and a coating layer coating the nuclear particles, wherein the nuclear particles are composed of a drug, a first nuclear-particle component, a second nuclear-particle component and a surfactant, the drug is an aniline derivative represented by the following general formula (I):

[Formula 1]

(I)

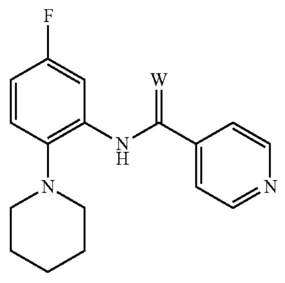

wherein W represents S or O, or a pharmaceutically acceptable salt thereof, or a hydrate thereof, the first nuclear-particle component is at least one crystalline cellulose having a shape selected from a needle-shape and a substantially columnar shape, and the second nuclear-particle component is at least one pharmaceutically acceptable additive having a substantially spherical shape.

[2] The pharmaceutical preparation according to [1], wherein the drug is an aniline derivative represented by the following formula (I-a):

[Formula 2]

(I-a)

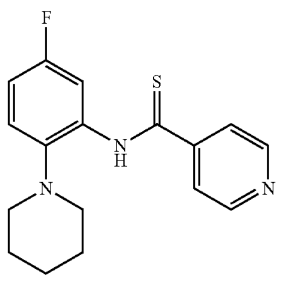

or a pharmaceutically acceptable salt, or a hydrate thereof.

[3] The pharmaceutical preparation according to [1] or [2], wherein an average aspect ratio of the first nuclear-particle component is 1.8 or more.

[4] The pharmaceutical preparation according to [3], wherein the average aspect ratio of the first nuclear-particle component is 1.8 to 10.0.

[5] The pharmaceutical preparation according to any one of [1] to [4], wherein an average aspect ratio of the second nuclear-particle component is 1.0 to 1.7.

[6] The pharmaceutical preparation according to [5], wherein the average aspect ratio of the second nuclear-particle component is 1.0 to 1.5.

[7] The pharmaceutical preparation according to any one of [1] to [6], wherein a ratio of a 50% particle size (D50) of the second nuclear-particle component based on volume distribution relative to a 50% particle size (D50) of the first nuclear-particle component based on volume distribution is 1:1.1 or less.

[8] The pharmaceutical preparation according to any one of [1] to [7], wherein a difference in average aspect ratio between the first nuclear-particle component and the second nuclear-particle component is 0.5 or more.

[9] The pharmaceutical preparation according to any one of [1] to [8], wherein the second nuclear-particle component is composed of at least two different components.

[10] The pharmaceutical preparation according to any one of [1] to [9], wherein a mass ratio of the first nuclear-particle component and the second nuclear-particle component is 1:1 to 1:10.

[11] The pharmaceutical preparation according to any one of [1] to [10], wherein a mass ratio of a total mass of the first nuclear-particle component and the second nuclear-particle component to a mass of the surfactant is 1:0.01 to 1:0.6.

[12] The pharmaceutical preparation according to any one of [1] to [11], wherein a mass ratio of the surfactant and the drug is 1:0.1 to 1:10.

[13] The pharmaceutical preparation according to any one of [1] to [12], wherein a mass ratio of the total mass of the first nuclear-particle component and the second nuclear-particle component and a mass of the coating layer is 1:0.05 to 1:0.3.

[14] The pharmaceutical preparation according to any one of [1] to [13], wherein the second nuclear-particle component is at least one pharmaceutically acceptable additive selected from the group consisting of sugars and inorganic compounds.

[15] The pharmaceutical preparation according to any one of [1] to [14], wherein the second nuclear-particle component is at least one selected from the group consisting of glucose, fructose, lactose, lactose hydrate, sucrose, white sugar, compressed sugar, refined sugar powder, ammonium alginate, starch, potato starch, wheat starch, corn starch, rice starch, mannitol, sorbitol, phosphate, magnesium carbonate, magnesium oxide, calcium carbonate, sulfuric acid calcium, dextrates, dextrin, dextrose, polymethacrylate, glycerin palmitostearate, isomaltose, lactitol, kaolin, lactitol, maltitol, maltodextrin, maltose, trehalose, xylitol, gelatinized starch, modified gelatinized starch, tapioca starch and sodium chloride.

[16] The pharmaceutical preparation according to any one of [1] to [15], wherein the surfactant is a nonionic surfactant.

[17] The pharmaceutical preparation according to [16], wherein the nonionic surfactant is polysorbate.

[18] The pharmaceutical preparation according to any one of [1] to [17], wherein the coating layer contains a water-soluble coating agent.

[19] The pharmaceutical preparation according to [18], wherein the water-soluble coating agent is at least one component selected from the group consisting of a polyalkylene glycol, a polysaccharide, and derivatives thereof.

[20] The pharmaceutical preparation according to [18] or [19], wherein the water-soluble coating agent is at least one selected from the group consisting of polyethylene glycol, methyl cellulose, hydroxymethyl cellulose, hydroxypropyl cellulose, hydroxypropyl methylcellulose, a methacrylic acid copolymer, a vinylpyridine copolymer, an alkyl vinylpyridine copolymer, an amino cellulose derivative, diethylaminoethyl methacrylate, polyvinylacetal diethyl aminoacetate, a dimethylaminoethyl methacrylate-methacrylate copolymer, cellulose acetate-N,N-di-n-butyl hydroxylpropyl ether, a copolymer of vinylpyridine and an acrylic acid series free acid, a copolymer of an alkyl vinylpyridine and an acrylic acid series free acid, a copolymer of vinylpyridine, an acrylic acid series free acid and a vinyl monomer, a copolymer of an alkyl vinylpyridine, acrylic acid series free acid and a vinyl monomer, a 2-methyl-5-vinylpyridine-methacrylic acid copolymer, poly-2-(vinyl phenyl)glycine, a morpholine-N-β-ethyl acrylate-methacrylic acid copolymer, shellac, cellulose acetate phthalate, a methyl acrylate-methacrylic acid copolymer, a methyl methacrylate-methacrylic acid copolymer, zein, hydroxypropyl methylcellulose phthalate and an aminoalkyl methacrylate copolymer.

[21] The pharmaceutical preparation according to any one of [1] to [20], wherein an agglomeration degree of the pharmaceutical preparation is 70% or less.

[22] The pharmaceutical preparation according to any one of [1] to [21], wherein the agglomeration degree of the pharmaceutical preparation is lower than an agglomeration degree of the nuclear particles.

[23] The pharmaceutical preparation according to any one of [1] to [22], wherein a 50% particle size (D50) of the pharmaceutical preparation based on volume distribution is 100 to 400 μm.

[24] A preparation containing the pharmaceutical preparation according to any one of [1] to [23] and having a dosage form selected from the group consisting of a granule, a tablet, a capsule, a powder and a pill.

[25] A method for producing a pharmaceutical preparation in the form of granules having nuclear particles and a coating layer coating the nuclear particles, including:

(a) mixing a first nuclear-particle component and a second nuclear-particle component to obtain a nuclear particle mixture, (b) dissolving or suspending a drug in a mixture of a surfactant and a solvent to obtain a mixed solution, (c) contacting the nuclear particle mixture obtained in (a) with the mixture obtained in (b) to obtain nuclear particles containing the first nuclear-particle component, second nuclear-particle component, drug and surfactant, and (d) coating the nuclear particles obtained in (c) to obtain a pharmaceutical preparation, wherein the drug is an aniline derivative represented by the following general formula (I):

[Formula 3]

(I)

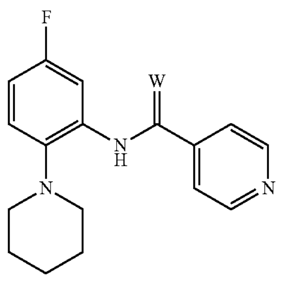

wherein W represents S or O, or a pharmaceutically acceptable salt thereof, or a hydrate thereof, the first nuclear-particle component is at least one crystalline cellulose having a shape selected from a needle-shape and a substantially columnar shape, and the second nuclear-particle component is at least one pharmaceutically acceptable additive having a substantially spherical shape.

[26] The production method according to [25], wherein the drug is an aniline derivative represented by the following formula (I-a):

[Formula 4]

(I-a)

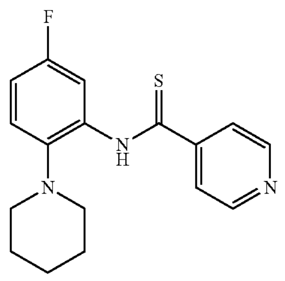

or a pharmaceutically acceptable salt thereof, or a hydrate thereof.

[27] The production method according to [25] or [26], wherein an average aspect ratio of the first nuclear-particle component is 1.8 or more.

[28] The production method according to [27], wherein the average aspect ratio of the first nuclear-particle component is 1.8 to 10.0.

[29] The production method according to any one of [25] to [28], wherein an average aspect ratio of the second nuclear-particle component is 1.0 to 1.7.

[30] The production method according to [29], wherein the average aspect ratio of the second nuclear-particle component is 1.0 to 1.5.

[31] The production method according to any one of [25] to [30], wherein a ratio of 50% particle size (D50) of the second nuclear-particle component based on volume distribution relative to the 50% particle size (D50) of the first nuclear-particle component based on volume distribution is 1:1.1 or less.

[32] The production method according to any one of [25] to [31], wherein the second nuclear-particle component is composed of at least two different components.

[33] The production method according to any one of [25] to [32], further including (e) obtaining a granular preparation by adding a pharmaceutically acceptable additive to the pharmaceutical preparation obtained in (d).

[34] The production method according to any one of [25] to [32], further including (e') obtaining a capsule-like preparation by enclosing the pharmaceutical preparation obtained in (d) with a film made of gelatin or a plant derived material.

[35] A method for producing tablets, including tableting the pharmaceutical preparation according to any one of [1] to [23].

[36] A method for producing capsules, including encapsulating the pharmaceutical preparation according to any one of [1] to [23].

According to the present invention, it is possible to provide a pharmaceutical preparation in the form of granules containing a therapeutically effective amount of a drug and having excellent flowability sufficient for practical production. According to the present invention, it is possible to suppress agglomeration which reduces flowability of a pharmaceutical preparation. As a result, the pharmaceutical preparation having excellent flowability is realized. Because of this, a poorly water-soluble component can be blended in a large amount in a pharmaceutical preparation such as tablets (tablet formation is inhibited by low flowability). Furthermore, even if the pharmaceutical preparation of the present invention is stored for a long time, it is possible to suppress leakage of the surfactant contained in nuclear particles to the surface of the pharmaceutical preparation.

BRIEF DESCRIPTION OF THE DRAWINGS

FIG. 1A and FIG. 1B show electron micrographs of a first nuclear-particle component (needle-like crystalline cellulose). FIG. 1A shows an electron micrograph of a needle-like crystalline cellulose (CEOLUS KG-1000), FIG. 1B shows an electron micrograph of a needle-like crystalline cellulose (CEOLUS UF-702).

FIG. 2 shows an electron micrograph of a second nuclear-particle component (substantially spherical particles: lactose hydrate).

FIG. 3 shows an electron micrograph of a second nuclear-particle component (substantially spherical particles: corn starch).

DETAILED DESCRIPTION OF THE INVENTION

Now, the present invention will be more specifically described. Note that, in the specification, the numerical range expressed by "to" means the range including numerical values before and after "to" as the minimum value and the maximum value, respectively. In the specification, the expression of "A or B" means that either one or both of A and B are included unless otherwise specified and except the case where interpreted in a limited way from the context.

[Pharmaceutical Preparation]

The pharmaceutical preparation of the present invention is a pharmaceutical preparation in the form of granules having nuclear particles and a coating layer coating the nuclear particles. The nuclear particles and coating layer will be individually described below.

<Nuclear Particles>

The nuclear particles are composed of a drug, a first nuclear-particle component, a second nuclear-particle component and a surfactant. The first nuclear-particle component is needle-like and/or substantially columnar crystalline cellulose (hereinafter sometimes simply referred to as "needle-like crystalline cellulose"). The second nuclear-particle component is at least one pharmaceutically acceptable additive having a substantially spherical shape.

Since the nuclear particles contain a first nuclear-particle component and a second nuclear-particle component significantly different in shape, many voids can be formed between the first nuclear-particle component and the second nuclear-particle component. As a result, the surface area in which a liquid component is internally contained increases in the nuclear particles. Because of this, a large amount of the liquid component can be contained in the nuclear particles. Also, since the nuclear particles can contain a large amount of a surfactant serving as a solubilizer as the liquid component, a poorly water-soluble drug can be dissolved or suspended. Although not bound by a theory, it is considered that a pharmaceutical preparation containing a large amount of a poorly water-soluble drug in nuclear particles can be produced based on such a mechanism.

(First Nuclear-Particle Component)

According to an embodiment of the present invention, the first nuclear-particle component to be used in nuclear particles is needle-like crystalline cellulose. The needle-like crystalline cellulose serving as the first nuclear particle of the present invention is derived from crystalline cellulose that can be added for preparing a pharmaceutical preparation. The needle-like crystalline cellulose is sufficient as long as it contains a needle-like and/or substantially columnar crystal in a rate sufficient for producing the effect of the present invention. The lower limit of the rate of the needle-like and/or substantially columnar crystalline cellulose in the first nuclear-particle component, although it is not particularly limited, is preferably 60%, more preferably 70%, and further more preferably 80%. The upper-limit thereof can be, for example, 100%, 98%, 95% and 90%. Although the range of the rate of the needle-like and/or substantially columnar crystalline cellulose in the first nuclear-particle component is not particularly limited, the range of the number of crystalline particles is preferably 60 to 100%, more preferably 70 to 100%, and further more preferably 80 to 100%. In the specification, the "needle-like crystalline cellulose" refers to crystalline cellulose having a significant difference between vertical and horizontal lengths in a longitudinal cross section of crystalline cellulose microscopic image (projected on a plane). The significant difference between vertical and horizontal lengths herein can be expressed by, for example, an aspect ratio.

More specifically, the average aspect ratio of the first nuclear-particle component, although it is not particularly limited as long as the effect of the present invention is produced, is larger than the average aspect ratio of the second nuclear-particle component. The lower limit thereof is preferably 1.8, more preferably 2.2, and further more preferably 2.5. The upper limit of the average aspect ratio of the first nuclear-particle component, although it is not particularly limited as long as the effect of the present invention is produced, can be, for example, 10 or 8. The range of the average aspect ratio of the first nuclear-particle component, although it is not particularly limited, is preferably 1.8 to 10, more preferably 2.2 to 10, and further more preferably 2.5 to 10. In the specification, the "aspect ratio" of a nuclear-particle component refers to the ratio of the major axis to the minor axis (longest diameter/shortest diameter) of a particle of a nuclear-particle component in a particle image obtained by electron microscopic analysis. The "average aspect ratio" of the nuclear-particle component refers to an average value of aspect ratios of particles of the nuclear-particle component, obtained by selecting 10 or more particles at random, measuring the aspect ratios of them, excluding the aspect ratio values of the top 10% and the bottom 10% and calculating an average of the remaining values.

The amount of the first nuclear-particle component, although it is not particularly limited as long as the effect of the present invention is produced, is preferably 5 to 50 mass % relative to the total mass of the pharmaceutical preparation.

(Second Nuclear-Particle Component)

According to an embodiment of the present invention, the second nuclear-particle component to be used in nuclear particles is a pharmaceutically acceptable additive having a substantially spherical shape. In the specification, the "substantially spherical" refers to a shape close to a sphere and having no significant difference between vertical and horizontal lengths in an electron microscopic image (projected on a plane). A needle-like shape and a substantially columnar shape are not included herein. In other words, the second nuclear-particle component according to an embodiment is a non-needle and non-columnar pharmaceutically acceptable additive. As to "substantially spherical" shape, the shape of an image observed by an electronic microscope may not be always a complete spherical shape and may be a distorted spherical, ellipsoidal, polyhedral (including a cube) and rounded polyhedral shape, for example.

The average aspect ratio of the second nuclear-particle component is smaller than the average aspect ratio of the first nuclear-particle component, preferably 1.0 to 1.65, more preferably 1.0 to 1.5, further more preferably 1.0 to 1.3, and still further more preferably 1.0 to 1.2. The aspect ratio and average aspect ratio of the second nuclear-particle component are the same as those of the first nuclear-particle component, respectively.

In the pharmaceutical preparation of the present invention, the amount of the second nuclear-particle component, although it is not particularly limited as long as the effect of the present invention is produced, is preferably 30 to 90 mass % relative to the total mass of the pharmaceutical preparation.

The particle size of the second nuclear-particle component, although it is not particularly limited as long as the effect of the present invention is produced, is controlled such that the 50% particle size (D50) of the second nuclear-particle component based on volume distribution relative to the 50% particle size (D50) of the first nuclear-particle component based on volume distribution (D50 of the first nuclear-particle component:D50 of the second nuclear-particle component based on volume distribution) becomes preferably 1:1.1 or less, more preferably 1:0.8 or less, further more preferably 1:0.5 or less, and still further preferably 1:0.1 or less.

As the second nuclear-particle component, a single type of component may be used alone and two or more types of components may be used in combination, and preferably two or more types of components different in D50 (50% particle size based on volume distribution) may be used in combination. For example, if the second nuclear-particle component is composed of two types of components, the D50 values (50% particle size based on volume distribution) of the two types of components preferably differ. Note that, in the present invention, if the nuclear-particle component contains two types or more components, 50% particle size (D50) of the nuclear-particle component based on volume distribution is calculated by calculating the mass ratios of individual components relative to the total mass of the components constituting the nuclear-particle component, obtaining products by multiplying the ratios of respective components by the D50 (50% particle size based on volume distribution) of respective components, and adding up the products. Assuming that the nuclear-particle component contains two types of components, A and B having a and b as a mass, respectively and $D50_A$ and $D50_B$ as D50 (the 50% particle sizes based on volume distribution), respectively, D50 (the 50% particle size based on volume distribution) of the nuclear-particle component can be calculated in accordance with the following equation:

[Expression 1]

$$D50\ \text{(50\% particle size based on volume distribution) of the nuclear-particle component} = \frac{a}{a+b} \times D50_A + \frac{b}{a+b} \times D50_B$$

The component (s) constituting the second nuclear-particle component, which are not particularly limited as long as they are pharmaceutically acceptable components, includes, for example, sugars (e.g., sugar, a sugar hydrate, a sugar alcohol) and inorganic compounds.

Examples of the sugars include, but are not particularly limited to, monosaccharides such as glucose, disaccharides such as lactose and sucrose, and polysaccharides such as starch. Examples of the starch include potato starch, wheat starch, corn starch and rice starch. As the sugar, preferably corn starch is used.

Examples of the sugar hydrate include, but are not particularly limited to, any hydrates of the aforementioned sugars. Preferably, a lactose hydrate is used.

Examples of the sugar alcohol include, but are not particularly limited to, sugar alcohols of any sugars. Preferably, mannitol or sorbitol is used.

Examples of the inorganic compounds include, but are not particularly limited to, phosphates such as anhydrous calcium phosphate.

The first nuclear-particle component has a larger average aspect ratio than the second nuclear-particle component. The difference in average aspect ratio between the first and second nuclear-particle components is preferably large. More specifically, the difference in average aspect ratio between the first and second nuclear-particle components (the average aspect ratio of the first nuclear-particle component−the average aspect ratio of the second nuclear-particle component) is preferably 0.5 or more, more preferably 0.6 or more, and further more preferably 0.7 or more.

The difference (tapped bulk density-poured bulk density) between the tapped bulk density and poured bulk density of a mixture (nuclear particle mixture) containing the first and second nuclear-particle components, is not particularly limited as long as the effect of the present invention is produced. The lower limit thereof is preferably 0.15, more preferably 0.16, and further more preferably 0.17, whereas, the upper limit is preferably 0.25, more preferably 0.24, and further more preferably 0.23. The range of the difference is preferably 0.15 to 0.25, more preferably 0.16 to 0.24, and further more preferably 0.17 to 0.23. Note that, in the present invention, the tapped bulk density and poured bulk density can be measured, for example, by a commercially available powder characteristics tester (Powder tester (registered trademark) PT-R, manufactured by HOSOKAWA MICRONE CORPORATION). The measuring method using Powder tester is specifically described in the 17th revised Japanese Pharmacopoeia. More specifically, a nuclear particle mixture is uniformly supplied, from above through a sieve, to a cylindrical vessel having the same dimensions as the measuring vessel, which are defined in Method 3 (bulk density and tapped density measurement method) described in the 17th revised Japanese Pharmacopoeia. The excess nuclear particle mixture is scraped from the top of the vessel and then the mixture is weighed. In this manner, the bulk density (poured bulk density) of the mixture roughly packed is measured. Then, an auxiliary cylinder is put on the vessel, and then, the nuclear particle mixture is added up to the level of the upper edge of the auxiliary cylinder and tapped 180 times. After completion of tapping, the auxiliary cylinder is removed. The excess particle mixture was scraped from the top of the vessel and the mixture is weighed. In this manner, the bulk density (tapped bulk density) of the mixture densely packed by tapping is measured.

The particle sizes (diameters) of particles constituting the first and second nuclear-particle component are not particularly limited as long as the effect of the present invention is produced. The D50 (50% particle size based on volume distribution) of the first nuclear-particle component is preferably 50 to 200 μm, more preferably 60 to 150 μm, and further more preferably 70 to 100 μm. The D50 (50% particle size based on volume distribution) of the second nuclear-particle component is preferably 1 to 300 μm, more preferably 5 to 200 μm, and further more preferably 10 to 150 μm. In the present invention, the diameter of the particles constituting a nuclear-particle component and 50% particle size based on volume distribution can be both measured by use of, for example, a commercially available particle size distribution meter (for example, Mastersizer 3000, manufactured by Spectris) in accordance with the laser diffractometry (measuring method: dry system, scattering intensity: 1% or more, light scattering model: Mie scattering theory). Note that, the D50 (50% particle size based on volume distribution) refers to the particle size corresponding to 50% in volume in the cumulative volume distribution curve (total volume: 100%) showing the volume-based particle size distribution, obtained by measurement in accordance with the laser diffractometry.

The total mass of the first and second nuclear-particle components, although it is not particularly limited as long as the effect of the present invention is produced, is for example, 20 to 90 wt % relative to the total mass of the pharmaceutical preparation.

The mass ratio of the first nuclear-particle component and the second nuclear-particle component (mass of the first nuclear-particle component:mass of the second nuclear-particle component), although it is not particularly limited as long as the effect of the present invention is produced, is, for example, 1:1 to 1:10.

(Surfactant)

The pharmaceutical preparation of the present invention contains a surfactant that can dissolve or suspend a drug in nuclear particles. The surfactant is not particularly limited as long as it is pharmaceutically acceptable. For example, a cationic surfactant, an anionic surfactant, an amphoteric surfactant and a nonionic surfactant can be used. Examples of the cationic surfactant include, a primary amine salt, an alkyltrimethylammonium salt, an alkylpyridinium salt and an alkyl polyoxyethylene amine. Examples of the anionic surfactant include a fatty acid salt, a rosin salt, an alkyl polyoxyethylene sulfate, an α-olefin sulfonate, an alkylnaphthalene sulfonate, a lignin sulfonate and an alkyl phosphate. Examples of the amphoteric surfactant include an N-alkyl β-amino propionate, an N-alkyl sulfobetaine, an N-alkyl hydroxysulfobetaine and lecithin. Examples of the nonionic surfactant include an alkyl polyoxyethylene ether, a polyoxyethylene fatty acid ester, a sorbitan fatty acid ester, a sucrose fatty acid ester, a polyglycerin fatty acid ester and a polyoxyethylene sorbitan fatty acid ester. Of them, the surfactant is preferably a nonionic surfactant, more preferably, a polysorbate, and further more preferably, polysorbate 80. These surfactants may be used alone or in combination of two or more. The surfactant may be dissolved in, for example, water or an alcohol, and put in use.

The amount of the surfactant is not particularly limited as long as the effect of the present invention is produced. The lower limit of the mass ratio of the surfactant relative to the total amount of the nuclear-particle components (the total mass of the nuclear-particle components: the mass of surfactant) is preferably 1:0.001, and more preferably 1:0.01. The upper limit thereof, although it is not particularly limited, is preferably 1:0.6, more preferably 1:0.4, and further more preferably 1:0.3. The range of the mass ratio of the surfactant relative to the total amount of nuclear-particle components, although it is not particularly limited, is preferably 1:0.001 to 1:0.6, more preferably 1:0.01 to 1:0.4, and further more preferably 1:0.01 to 1:0.3.

(Drug)

The pharmaceutical preparation of the present invention contains, in the nuclear, an aniline derivative represented by the following general formula (I):

[Formula 5]

(I)

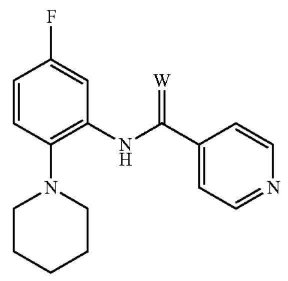

wherein W represents S or O, or a pharmaceutically acceptable salt thereof, or a hydrate thereof. The drug is preferably present in a dissolved or suspended state in a surfactant (hereinafter sometimes referred to as a "mixed solution") as mentioned above. Note that, in the specification, the case where a part of a drug is dissolved and another part of the drug is suspended is also included in the sense of "solvent or suspension".

As the drug represented by the general formula (I), specifically, N-[5-fluoro-2-(1-piperidinyl)phenyl]isonicotinethioamide (FIT-039) represented by the following formula (I-a) can be mentioned.

[Formula 6]

(I-a)

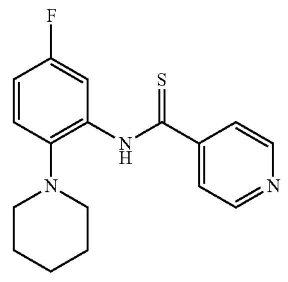

The pharmaceutical preparation of the present invention may contain another drug in addition to the aforementioned drug. Examples of the another drug may include an antiviral agent, an anti-inflammatory agent and an immunity enhancer.

In the pharmaceutical preparation of the present invention, the amount of the drug is not particularly limited as long as the pharmaceutical preparation of the present invention produces a desired effect. The lower limit of the mass ratio of the drug relative to the total amount of the nuclear-particle components (the mass of a drug: the total mass of the nuclear-particle components) is preferably 0.01:1, more preferably 0.02:1, and further more preferably 0.03:1. The upper limit thereof, although it is not particularly limited, is preferably 0.5:1, and more preferably 0.2:1. The range of mass ratio of the drug relative to the total amount of the nuclear-particle components, although it is not particularly limited, is preferably 0.01:1 to 0.5:1, more preferably 0.02:1 to 0.5:1, and further more preferably 0.03:1 to 0.2:1.

In the pharmaceutical preparation of the present invention, the amount of a drug is not particularly limited as long as the pharmaceutical preparation of the present invention produces a desired effect. The lower limit of a mass ratio of the drug to a surfactant (the mass of a drug:the mass of a surfactant) is preferably 0.05:1, more preferably 0.1:1, and further more preferably 0.5:1. The upper limit thereof, although it is not particularly limited, is preferably 5:1, and more preferably 3:1. The range of the mass ratio of a drug to a surfactant, although it is not particularly limited, is preferably 0.05:1 to 5:1, more preferably 0.1:1 to 5:1, and further more preferably 0.5:1 to 3:1.

In the pharmaceutical preparation of the present invention, the agglomeration degree of nuclear particles, although it is not particularly limited, is preferably 90% or less, more preferably 70% or less, and further more preferably 50% or less.

The agglomeration degree can be measured by using a commercially available powder characteristics tester. Examples of the powder characteristics tester include Powder tester (registered trademark) PT-R (manufactured by HOSOKAWA MICRONE CORPORATION). The measurement conditions are, for example, as follows.

Mesh opening: (upper stage) 710 μm, (middle stage) 355 μm, (lower stage) 250 μm

Sampling volume: 2 g or 3 g

Shaking time: 119 seconds

In the above conditions, the values of individual terms in the following equations are measured.

$$X=[\text{mass of powder remaining in upper stage}]/\text{the mass of powder loaded}\times 100$$

$$Y=[\text{mass of powder remaining in middle stage}]/\text{the mass of powder loaded}\times 100\times 0.6$$

$$Z=[\text{mass of powder remaining in lower stage}]/\text{the mass of powder loaded}\times 100\times 0.2$$

The total value of "X", "Y" and "Z" is used as an agglomeration degree (%).

<Coating Layer>

The coating layer coats nuclear particles to successfully suppress leakage of a surfactant and drug contained in nuclear particles to the surface of a pharmaceutical preparation. As a result that leakage of a surfactant is suppressed by a coating layer, agglomeration and a decrease in flowability of a pharmaceutical preparation can be suppressed.

The component(s) constituting the coating layer is not particularly limited; for example, a water-soluble coating agent may be mentioned. The water-soluble coating agents may be used alone or in combination of two or more.

According to an embodiment, the water-soluble coating agent contains preferably at least one component selected from a polyalkylene glycol and a polysaccharide or a derivative thereof.

The polysaccharide or a derivative thereof is preferably a cellulose derivative such as methyl cellulose, hydroxymethyl cellulose, hydroxypropyl methylcellulose. The cellulose derivatives may be used alone or in combination of two or more.

Examples of the polyalkylene glycol include polyethylene glycol.

According to another preferable embodiment, examples of the coating agent to be used in the coating layer include hydroxypropyl cellulose, hydroxypropyl methylcellulose, a methacrylic acid copolymer, a vinylpyridine copolymer, an alkyl vinylpyridine copolymer, amino cellulose derivative, diethylaminoethyl methacrylate, polyvinyl acetal diethylaminoacetate, a dimethylaminoethyl methacrylate-methacrylate copolymer, cellulose acetate-N,N-di-n-butyl hydroxylpropyl ether, a copolymer of vinylpyridine and an acrylic acid series free acid, a copolymer of an alkyl vinylpyridine and an acrylic acid series free acid, a copolymer of vinylpyridine, an acrylic acid series free acid and a vinyl monomer, a copolymer of an alkyl vinylpyridine, an acrylic acid series free acid and a vinyl monomer, 2-methyl-5-vinylpyridine-methacrylic acid copolymer, poly-2-(vinylphenyl)glycine, a morpholine-N-β-ethyl acrylate-methacrylic acid copolymer, shellac, cellulose acetate phthalate, a methyl acrylate-methacrylic acid copolymer, a methyl methacrylate-methacrylic acid copolymer, zein, hydroxypropyl methylcellulose phthalate and an aminoalkyl methacrylate copolymer. These may be used alone or in combination of two or more.

According to an embodiment, the coating agent may be used in combination with a plasticizer. Examples of the plasticizer include acetyl tributyl citrate, acetyl triethyl citrate, castor oil, diacetylated monoglyceride, dibutyl sebacate, sorbitol, dextrin, diethyl phthalate, glycerin, polyalkylene glycol, polyethylene glycol monoethyl ether, propylene glycol, benzyl benzoate, purified water, sorbitol, a sorbitan solution, triacetin, tributyl citrate, triethyl citrate and chlorobutanol. Of these plasticizers, preferably a polyalkylene glycol, and more preferably polyethylene glycol (macrogol) is used. These plasticizers may be used alone or in combination of two or more.

The component constituting the coating layer may be directly used or, if necessary, dissolved in, e.g., water or an alcohol, and put in use.

In the pharmaceutical preparation of the present invention, the amount of the coating layer is not particularly limited as long as the pharmaceutical preparation of the present invention produces a desired effect. The lower limit of the ratio of the mass of the coating layer relative to the total mass of nuclear particles (the mass of the coating layer:total mass of nuclear particles) is preferably 0.001:1, and more preferably 0.002:1. The upper limit thereof, although it is not particularly limited, is preferably 0.1:1, more preferably 0.05:1, and further more preferably 0.02:1. The range of the ratio of the mass of the coating layer relative to the total mass of the nuclear particles, although it is not particularly limited, is preferably 0.001:1 to 0.1:1, more preferably 0.002:1 to 0.05:1, and further more preferably 0.002:1 to 0.02:1.

<Other Components>

The pharmaceutical preparation of the present invention may contain pharmaceutically acceptable additives, which are different from components constituting the nuclear particles and the coating layer, as long as the effect of the present invention is not prevented. Examples of the additives include an excipient, a disintegrant, a lubricant, a binder, a fluidizer, a sweetener, a fragrance and a coloring agent. These additives may have two functions per agent and may be used alone or in combination of two or more.

Since the pharmaceutical preparation of the present invention has a coating layer that covers nuclear particles, leakage of a surfactant and a drug contained in the nuclear particles from the pharmaceutical preparation is suppressed. As a result, agglomeration of the pharmaceutical preparation can be suppressed.

The agglomeration degree of the pharmaceutical preparation is preferably 70% or less, more preferably 60% or less, and further more preferably 50% or less. The measurement of agglomeration degree of the pharmaceutical preparation can be carried out in the same manner as in the aforementioned measurement of agglomeration degree of nuclear particles.

It is preferable that the agglomeration degree of the pharmaceutical preparation is better (lower) than that of the nuclear particles.

The particle size of the pharmaceutical preparation is not particularly limited. The D50 (50% particle size based on volume distribution) is 100 to 400 μm, and more preferably 120 to 250 μm. Measurement of 50% particle size (D50) of a pharmaceutical preparation based on volume distribution is carried out in the same manner as in the aforementioned measurement of a nuclear-particle component.

The pharmaceutical preparation of the present invention may be directly used or may be processed into various dosage forms. The dosage form of the pharmaceutical preparation is not particularly limited as long as the effect of the present invention is produced. Examples of the dosage form include granules, tablets, pills, capsules and powders. Of them, granules, tablets and capsules are preferred. As the capsules, hard capsules are mentioned.

[Method for Producing Pharmaceutical Preparation]

A method for producing the pharmaceutical preparation of the present invention is not particularly limited and a method known in the technical field can be used. Production conditions for the pharmaceutical preparation may be appropriately controlled depending on the types of nuclear-particle components, surfactant, drug and coating-layer components. As the drug, a drug represented by the above general formula (I) is used. More specifically, the pharmaceutical preparation of the present invention can be produced, for example, in accordance with the following procedure. First, a first nuclear-particle component, i.e., needle-like and/or substantially columnar crystalline cellulose, and a second nuclear-particle component, i.e., at least one pharmaceutically acceptable additive having a substantially spherical shape, are mixed by use of a fluidized bed granulator (for example, FD-MP-01D, manufactured by Powrex Corp.) to obtain a nuclear particle mixture (primary particles). Separately, a drug is added to a surfactant and stirred by a mixer (NZ-1200, manufactured by TOKYO RIKAKIKAI CO, LTD.) to obtain a mixed solution (drug solution) in which the drug is dissolved or suspended. Then, the obtained mixture and the mixed solution are brought into contact with each other by use of a fluidized bed granulator to attach the mixed solution to the nuclear particles (in the mixture) to obtain nuclear particles. Contact between the mixture and the mixed solution is carried out by a method, e.g., spraying the mixed solution to the mixture, or dipping the mixture in the mixed solution. Subsequently, a nuclear-particle component is dried as needed, and then, the nuclear particles are coated with a component (coating-layer component) constituting a coating layer. The coating of the nuclear particles is formed by a method, e.g., spraying the coating-layer component to the nuclear particles, or dipping the nuclear particles in (a solution of) the coating-layer component. Then, particles composed of nuclear particles and a coating layer that coats the nuclear particles, are dried to obtain a pharmaceutical preparation.

A method for tableting the pharmaceutical preparation is not particularly limited and a method known in the technical field can be used. The conditions for tableting are not particularly limited and can be appropriately controlled depending on, e.g., the types of nuclear-particle components, surfactant, drug and coating-layer components. As a method for tableting the pharmaceutical preparation, for example, a method of tableting the pharmaceutical preparation by a tablet press such as a rotary tablet press or a single-shot tablet press. Of them, a method of tableting the pharmaceutical preparation by a rotary tablet press is preferred. As the rotary tablet press, e.g., VIRGO 0512SS2AY manufactured by KIKUSUI is mentioned. If tablets contain pharmaceutically acceptable additive(s) other than the pharmaceutical preparation of the present invention, the pharmaceutical preparation of the present invention and the pharmaceutically acceptable additive(s) are first mixed and then tableted. A method for mixing the pharmaceutical preparation and additives is not particularly limited and a method known in the technical field can be used. As the method for mixing the pharmaceutical preparation and additives, for example, a method of using a mixer such as a V-shape mixer, is mentioned. More specifically, the V-shape mixer (TCV-20) manufactured by TOKUJU CORPORATION can be used for mixing.

A method for encapsulating the pharmaceutical preparation is not particularly limited and a method known in the technical field can be used. More specifically, the pharmaceutical preparation is encapsuled by putting the preparation in a capsule formed of a film of, e.g., gelatin, or plant-derived material. A method for putting the preparation in the capsule formed of a film is not particularly limited and a method known in the technical field such as auger powder filling, die-compress system powder filling and vibration type powder filling, can be employed. For example, in the auger powder filling, powdery or granular pharmaceutical preparation supplied/dropped from a hopper into cap-shaped containers each having an open end and usually formed of a gelatin film, and directly put in capsule bodies in a predetermined amount by use of a stirring blade and rotation pressure of an auger, and then, the cap-shaped containers are coaxially joined to produce capsules.

Examples

Now, the present invention will be more specifically described based on the following Examples, but the present invention is not limited to these Examples. Note that, in the Examples, the "average particle size (D50)" means "50% particle size based on volume distribution", unless otherwise specified.

[Method for Preparing Nuclear Particles]

A lactose hydrate (SuperTab (registered trademark), average particle size (D50): 120 μm, manufactured by DFE Pharma) and corn starch (defined by the Japanese Pharmacopoeia, average particle size (D50): 15 μm, manufactured by Nihon Shokuhin Kako Co., Ltd.) were prepared as the substantially spherical particles; and crystalline cellulose (CEOLUS UF-702, average particle size (D50): 140 μm, manufactured by Asahi Kasei Corporation), and crystalline cellulose (CEOLUS KG-1000, average particle size (D50): 80 μm, manufactured by Asahi Kasei Corporation) were prepared as the needle-like and/or substantially columnar crystalline cellulose. Image measurement of these was carried out by an electronic microscope (VE-7800, manufactured by KEYENCE). FIGS. 1A and B show electron micrographs of the needle-like and/or substantially columnar crystalline cellulose, CEOLUS KG-1000 and CEOLUS UF-702, respectively. FIG. 2 shows an electron micrograph of a lactose hydrate (substantially spherical particles). FIG. 3 shows an electron micrograph of corn starch (substantially spherical particles).

In accordance with the prescriptions shown in Table 1, a lactose hydrate (SuperTab (registered trademark), average aspect ratio 1.39, average particle size (D50): 120 μm, manufactured by DFE Pharma), and corn starch (defined by the Japanese Pharmacopoeia, average aspect ratio: 1.23, average particle size (D50): 15 μm, manufactured by Nihon Shokuhin Kako Co., Ltd.) as the substantially spherical particles; crystalline cellulose (CEOLUS UF-702, average aspect ratio: 2.63, average particle size (D50): 140 μm, manufactured by Asahi Kasei Corporation), and (CEOLUS KG-1000, average aspect ratio: 4.20, average particle size (D50): 80 μm, manufactured by Asahi Kasei Corporation) as the needle-like crystalline cellulose, were separately sieved through a 355 μm-sieve, put in a polyethylene bag and premixed. Note that, the average aspect ratio of each nuclear-particle component was measured by obtaining particle images by an electronic microscope (VE-7800, manufactured by KEYENCE) and analyzing the images; more specifically, selecting 10 particles from the images, measuring the aspect ratios of the 10 particles, removing aspect ratio values of top 10% and bottom 10% and averaging the remaining aspect ratio values. In Table 1, the unit of numerical values is gram (g), unless otherwise specified.

TABLE 1

| Test example | | | Comparative Example 1 | Example 1 | Example 2 | Example 3 |
|---|---|---|---|---|---|---|
| Nuclear particle | First nuclear-particle component | Crystalline cellulose (CEOLUS UF-702) | — | 125 | 62.5 | 125 |
| | Second nuclear-particle component | Corn starch | 125 | 125 | 62.5 | 125 |
| | | Lactose hydrate (Super Tab) | 125 | — | 417.5 | 187.5 |
| | Surfactant | Polysorbate 80 | 75 | 75 | 25 | 150 |
| | Solvent | Ethanol | 300 | 300 | 200 | 300 |
| | Drug | FIT-039CT | 31.25 | 31.25 | 62.5 | 125 |
| Coating layer | Coating agent | Hypromellose 2910 (TC-5E) | 16 | 16 | 1.24 | 32 |
| | | Macrogol 6000SP | 1.6 | 1.6 | 0.124 | 3.2 |
| | Solvent | Purified water | 232.4 | 232.4 | 308.6 | 284.8 |
| Pharmaceutical preparation (coated granules) | | | 373.85 | 373.85 | 631.364 | 747.7 |
| First nuclear-particle component D50:second nuclear-particle component D50 | | | — | 1:0.1 | 1:0.8 | 1:0.6 |

Then, the mixtures of Examples and Comparative Example were loaded in a fluidized bed granulator (FD-MP-01D, manufactured by Powrex Corp.) and a nuclear particle mixture (primary particles) was mixed (preheat step) in the conditions shown in Table 2.

TABLE 2

| <Preheat step> | | |
|---|---|---|
| Air supply temperature (° C.) | Air flow-rate ($m^3$/minute) | Mixing time (minutes) |
| 60 | 0.3 or more | 10 |
| <Granulation step> | | |
| Stirrer rotator rate | | |
| Rate preventing sedimentation | | |
| Air supply temperature (° C.) | Air flow-rate ($m^3$/minute) | Preheating time |
| 60 | 0.3 | Time to reach 60° C. |
| Opening degree of damper (°) | Spray pressure (MPa) | Spray flow-rate (L/minute) |
| 10 | 0.1 | 40 |
| Pump flow-rate (mL/minute) | Scraping time (seconds) | Interval time (seconds) |
| 7 | 0.3 | 40 |
| Spray amount (g/minute) | Product temperature (° C.) | Reference |
| 7 | About 30 | Confirmation of pressure damage of filter and product |

<Measurement of Bulk Density of Nuclear Particle Mixture>

The tapped bulk density and poured bulk density of each of the nuclear particle mixtures (primary particles), which were obtained in accordance with the prescriptions of Comparative Example 1 and Examples 1 and 2, were measured. More specifically, the bulk densities were measured by Powder tester (registered trademark) PT-R (manufactured by HOSOKAWA MICRONE CORPORATION) in accordance with Method 3 (described in the 17th revised Japanese Pharmacopoeia, as the bulk density and tapped density measurement). The nuclear particle mixture was uniformly supplied from above through a sieve to a cylindrical vessel having the same dimensions as the measuring vessel defined by Method 3. The excess nuclear particle mixture was scraped from the top of the vessel, and the mixture was weighed. In this manner, the bulk density (poured bulk density) of the mixture loosely packed was measured. Then, an auxiliary cylinder was put on the vessel, and then, the nuclear particle mixture was added up to the level of the upper edge of the auxiliary cylinder and tapped 180 times. After completion of tapping, the auxiliary cylinder was removed. The excess nuclear particle mixture was scraped from the top of the vessel, and the mixture was weighed. In this manner, the bulk density (tapped bulk density) of the mixture densely packed by tapping was measured. Then, difference between the tapped bulk density and the poured bulk density of each of the nuclear particle mixtures (tapped bulk density-poured bulk density) was calculated. The results are shown in Table 3. Further, the tapped bulk density and poured bulk density of the nuclear particle mixture (primary particles), which was obtained in accordance with the prescription of Example 3, were measured in the same manner as mentioned above. The difference (tapped bulk density-poured bulk density) between the tapped bulk density and the poured bulk density of the nuclear particle mixture of Example 3 was 0.221.

TABLE 3

| Test case | Comparative Example 1 | Example 1 | Example 2 |
|---|---|---|---|
| Agglomeration degree before coating (%) | 24.1 | 42.3 | 84.6 |
| Agglomeration degree after coating (%) | — | 17.5 | 16.3 |
| Tapped bulk density-poured bulk density of nuclear particle mixture (g/cc) | 0.295 | 0.218 | 0.221 |
| Granular particles were produced or not | x | ○ | ○ |
| Tablets were produced or not | x | ○ | ○ |

In accordance with each of the prescriptions shown in Table 1, a surfactant was added in a 500-mL beaker and mixed/stirred by a mixer (NZ-1200, manufactured by TOKYO RIKAKIKAI CO, LTD.) at a rate of 400 to 900 rpm. After the mixture was stirred until homogeneous state, the drug was added and further stirred/mixed to obtain a drug solution.

Then, the drug solution was sprayed to each of the nuclear particle mixtures (primary particles) obtained in the above by use of a fluidized bed granulator (FD-MP-01D, manufactured by Powrex Corp.) to obtain nuclear particles, i.e., primary particles attached with the drug solution (granulation step). The conditions of the fluidized bed granulator were set as shown in Table 2.

<Measurement Agglomeration Degree of Nuclear Particles>

Agglomeration degrees of the nuclear particles of the pharmaceutical preparations obtained in Examples 1 and 2, and Comparative Example were evaluated by use of a powder characteristics evaluation device (Powder tester (registered trademark) PT-R, manufactured by HOSOKAWA MICRONE CORPORATION). The conditions of the powder characteristics tester were set as shown below.

Mesh opening: (upper stage) 710 μm, (middle stage) 355 μm, (lower stage) 250 μm

Sampling volume: 2 g or 3 g

Shaking time: 119 seconds

The terms of the following equations were measured in the above conditions.

$$X=[\text{mass of powder remaining in upper stage}]/\text{the mass of powder loaded}\times 100$$

$$Y=[\text{mass of powder remaining in middle stage}]/\text{the mass of powder loaded}\times 100\times 0.6$$

$$Z=[\text{mass of powder remaining in lower stage}]/\text{the mass of powder loaded}\times 100\times 0.2$$

The total value of "X", "Y" and "Z" was used as an agglomeration degree (%). The results are shown in Table 3.

The coating-layer components according to each of the prescriptions shown in Table 1 were put in a stainless-steel vessel and stirred/mixed by a mixer (NZ-1200, manufactured by TOKYO RIKAKIKAI CO, LTD.) at a rate of 400 to 900 rpm to obtain coating layer solutions.

Then, the coating layer solutions were sprayed to corresponding nuclear particles obtained above by use of a fluidized bed granulator (FD-MP-01D, manufactured by Powrex Corp.) and dried at 60° C. for 15 minutes to obtain pharmaceutical preparations having nuclear particles coated with the coating layer solution. The conditions of the fluidized bed granulator were set as shown in Table 4.

TABLE 4

| <Coating step> | | |
|---|---|---|
| Rotation rate of stirrer | | |
| Rate preventing sedimentation | | |
| Air supply temperature (° C.) | Air flow-rate ($m^3$/minute) | Preheating time |
| 80 | 0.3 | — |
| Opening degree of damper (°) | Spray pressure (MPa) | Spray flow-rate (L/minute) |
| 10 | 0.1 | 40 |

TABLE 4-continued

| <Coating step> | | |
|---|---|---|
| Pump flow-rate (mL/minute) | Scraping time (seconds) | Interval time (seconds) |
| 4 | 0.3 | 4 |
| Spray amount (g/minute) | Product temperature (° C.) | Reference |
| 4 | About 30 | Confirmation of pressure damage of filter and product |

The agglomeration degrees of the pharmaceutical preparations obtained in Example 1 and 2, and Comparative Example 1 were measured in the same manner as in the aforementioned measurement for nuclear particles. The results are shown in Table 3.

As is apparent from the results of Table 3, since the pharmaceutical preparation according to the prescription of Comparative Example 1 (using a second nuclear-particle component alone was used as a nuclear-particle component) was significantly agglomerated, the agglomeration degree of the pharmaceutical preparation (agglomeration degree after coating) was not measured. In addition, the pharmaceutical preparation according to the prescription of Comparative Example 1 was produced neither into granular form nor tablets. In contrast, the pharmaceutical preparations according to the prescriptions of Examples 1 and 2 (using a first nuclear-particle component (crystalline cellulose) and a second nuclear-particle component are used in combination for a nuclear-particle component), had satisfactory flowability since agglomeration of the preparation was suppressed. In addition, the pharmaceutical preparations according to the prescriptions of Examples 1 and 2 were produced into granules and successfully formed into tablets by tableting. Similarly, granules and tablets were successfully obtained from the pharmaceutical preparation according to the prescription of Example 3. Also, it was confirmed that pharmaceutical preparations according to Examples 1 to 3 produced in accordance with a prescription in which the blending ratio of the first and second nuclear-particle components was changed (first nuclear-particle component D50: second nuclear-particle component D50 to 1:1.1) are suppressed in agglomeration and have satisfactory flowability. Note that, in the case where CEOLUS KG-1000 (average aspect ratio 4.20, average particle size (D50): 80 μm, manufactured by Asahi Kasei Corporation) was used as the first nuclear-particle component and the ratio of the first nuclear-particle component D50:second nuclear-particle component D50 was controlled to be 1:1.1 or less, it was confirmed that that agglomeration of the pharmaceutical preparation is suppressed and satisfactory flowability is obtained.

INDUSTRIAL APPLICABILITY

According to the present invention, it is possible to provide a pharmaceutical preparation containing a therapeutically effective amount of a poorly water-soluble drug (CDK9 inhibitor) and having excellent flowability sufficient for practical production.

The invention claimed is:

1. A pharmaceutical preparation in the form of granules comprising nuclear particles and a coating layer coating the nuclear particles, wherein the nuclear particles comprise a drug, a first nuclear-particle component, a second nuclear-particle component and a nonionic surfactant, the drug is an aniline derivative represented by the following general formula (I):

[Formula 1]

(I)

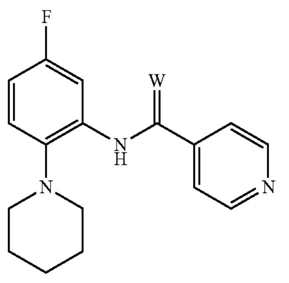

wherein W represents S or O, or a pharmaceutically acceptable salt thereof, or a hydrate thereof, the first nuclear-particle component is at least one crystalline cellulose having a shape selected from a needle-shape and a substantially columnar shape, and the second nuclear-particle component is at least one pharmaceutically acceptable additive having a substantially spherical shape, the nuclear particles are agglomerated particles formed from the first nuclear-particle component and the second nuclear-particle component, the nuclear particles have many voids formed between the first nuclear particle component and the second nuclear particle component, and a large amount of the drug and the surfactant are retained in the voids, wherein the surfactant is present as a liquid component, and at least one of the following conditions is satisfied: (i) a mass ratio of the first nuclear-particle component and the second nuclear-particle component is 1:1 to 1:10, (ii) an average aspect ratio of the first nuclear-particle component is 1.8 or more and an average aspect ratio of the second nuclear-particle component is 1.0 to 1.7, or (iii) the ratio of the needle-shape and/or a substantially columnar shape in the first nuclear particle component being 60 to 100%.

2. The pharmaceutical preparation according to claim 1, wherein the coating layer coats the nuclear particles.

3. The pharmaceutical preparation according to claim 1, wherein the drug is attached to at least a portion of a surface of at least one of the first nuclear-particle component and the second nuclear-particle component.

4. The pharmaceutical preparation according to claim 1, wherein the drug is an aniline derivative represented by the following formula (I-a):

[Formula 2]

(I-a)

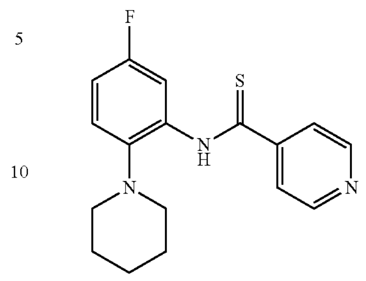

or a pharmaceutically acceptable salt, or a hydrate thereof.

5. The pharmaceutical preparation according to claim 1, wherein the drug and the surfactant are retained in the voids of the nuclear particles.

6. The pharmaceutical preparation according to claim 1, wherein an average aspect ratio of the first nuclear-particle component is 1.8 or more, and an average aspect ratio of the second nuclear-particle component is 1.0 to 1.7.

7. The pharmaceutical preparation according to claim 6, wherein the average aspect ratio of the first nuclear-particle component is 1.8 to 10.0.

8. The pharmaceutical preparation according to claim 6, wherein the average aspect ratio of the second nuclear-particle component is 1.0 to 1.5.

9. The pharmaceutical preparation according to claim 1, wherein a ratio of a 50% particle size (D50) of the second nuclear-particle component based on volume distribution relative to a 50% particle size (D50) of the first nuclear-particle component based on volume distribution is 1:1.1 or less.

10. The pharmaceutical preparation according to claim 1, wherein a difference in average aspect ratio between the first nuclear-particle component and the second nuclear-particle component is 0.5 or more.

11. The pharmaceutical preparation according to claim 1, wherein the second nuclear-particle component is composed of at least two different components.

12. The pharmaceutical preparation according to claim 1, wherein a mass ratio of the first nuclear-particle component and the second nuclear-particle component is 1:1 to 1:10.

13. The pharmaceutical preparation according to claim 1, wherein a mass ratio of a total mass of the first nuclear-particle component and the second nuclear-particle component to a mass of the surfactant is 1:0.01 to 1:0.6.

14. The pharmaceutical preparation according to claim 1, wherein a mass ratio of the surfactant and the drug is 1:0.1 to 1:10.

15. The pharmaceutical preparation according to claim 1, wherein a mass ratio of the total mass of the first nuclear-particle component and the second nuclear-particle component and a mass of the coating layer is 1:0.05 to 1:0.3.

16. The pharmaceutical preparation according to claim 1, wherein the second nuclear-particle component is at least one pharmaceutically acceptable additive selected from the group consisting of sugars and inorganic compounds.

17. The pharmaceutical preparation according to claim 1, wherein the second nuclear-particle component is at least one selected from the group consisting of glucose, fructose, lactose, lactose hydrate, sucrose, white sugar, compressed sugar, refined sugar powder, ammonium alginate, starch, potato starch, wheat starch, corn starch, rice starch, mannitol, sorbitol, phosphate, magnesium carbonate, magnesium oxide, calcium carbonate, sulfuric acid calcium, dextrates, dextrin, dextrose, polymethacrylate, glycerin palmitostearate, isomaltose, lactitol, kaolin, lactitol, maltitol, maltodextrin, maltose, trehalose, xylitol, gelatinized starch, modified gelatinized starch, tapioca starch and sodium chloride.

18. The pharmaceutical preparation according to claim 1, wherein the nonionic surfactant is polysorbate.

19. The pharmaceutical preparation according to claim 1, wherein the coating layer contains a water-soluble coating agent.

20. The pharmaceutical preparation according to claim 19, wherein the water-soluble coating agent is at least one component selected from the group consisting of a polyalkylene glycol, a polysaccharide, and derivatives thereof.

21. The pharmaceutical preparation according to claim 19, wherein the water-soluble coating agent is at least one selected from the group consisting of polyethylene glycol, methyl cellulose, hydroxymethyl cellulose, hydroxypropyl cellulose, hydroxypropyl methylcellulose, a methacrylic acid copolymer, a vinylpyridine copolymer, an alkyl vinylpyridine copolymer, an amino cellulose derivative, diethylaminoethyl methacrylate, polyvinylacetal diethyl aminoacetate, a dimethylaminoethyl methacrylate-methacrylate copolymer, cellulose acetate-N,N-di-n-butyl hydroxylpropyl ether, a copolymer of vinylpyridine and an acrylic acid series free acid, a copolymer of an alkyl vinylpyridine and an acrylic acid series free acid, a copolymer of vinylpyridine, an acrylic acid series free acid and a vinyl monomer, a copolymer of an alkyl vinylpyridine, acrylic acid series free acid and a vinyl monomer, a 2-methyl-5-vinylpyridine-methacrylic acid copolymer, poly-2-(vinyl phenyl)glycine, a morpholine-N-β-ethyl acrylate-methacrylic acid copolymer, shellac, cellulose acetate phthalate, a methyl acrylate-methacrylic acid copolymer, a methyl methacrylate-methacrylic acid copolymer, zein, hydroxypropyl methylcellulose phthalate and an aminoalkyl methacrylate copolymer.

22. The pharmaceutical preparation according to claim 1, wherein an agglomeration degree of the pharmaceutical preparation is 70% or less.

23. The pharmaceutical preparation according to claim 1, wherein an agglomeration degree of the pharmaceutical preparation is lower than an agglomeration degree of the nuclear particles.

24. The pharmaceutical preparation according to claim 1, wherein a 50% particle size (D50) of the pharmaceutical preparation based on volume distribution is 100 to 400 μm.

25. A preparation comprising the pharmaceutical preparation according to claim 1 and having a dosage form selected from the group consisting of a granule, a tablet, a capsule, a powder and a pill.

26. A method for producing the pharmaceutical preparation of claim 1 comprising:

(a) mixing a first nuclear-particle component and a second nuclear-particle component to obtain a nuclear particle mixture, (b) dissolving or suspending a drug in a mixture of a nonionic surfactant and a solvent to obtain a mixed solution, (c) contacting the nuclear particle mixture obtained in (a) with the mixture obtained in (b) to obtain nuclear particles containing the first nuclear-particle component, the second nuclear-particle component, the drug and the nonionic surfactant, wherein voids are formed between the first nuclear-particle component and the second nuclear-particle component, and the drug and the nonionic surfactant are incorporated into and retained within the voids, the surfactant being present as a liquid component, and (d) coating the nuclear particles obtained in (c) to obtain a pharmaceutical preparation, wherein the drug is an aniline derivative represented by the following general formula (I):

[Formula 3]

(I)

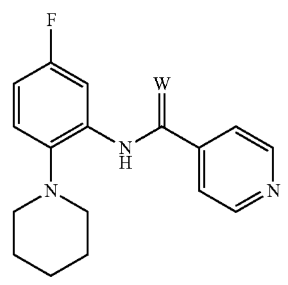

wherein W represents S or O, or a pharmaceutically acceptable salt thereof, or a hydrate thereof, the first nuclear-particle component is at least one crystalline cellulose having a shape selected from a needle-shape and a substantially columnar shape, and the second nuclear-particle component is at least one pharmaceutically acceptable additive having a substantially spherical shape, the nuclear particles have many voids formed between the first nuclear particle component and the second nuclear particle component, and are the nuclear particles capable of containing a large amount of the drug and the surfactant in the voids, wherein the surfactant is present as a liquid component, and at least one of the following conditions is satisfied: (i) a mass ratio of the first nuclear-particle component and the second nuclear-particle component is 1:1 to 1:10, (ii) an average aspect ratio of the first nuclear-particle component is 1.8 or more and an average aspect ratio of the second nuclear-particle component is 1.0 to 1.7, or (iii) the ratio of the needle-shape and/or a substantially columnar shape in the first nuclear particle component being 60 to 100%.

27. The production method according to claim 26, wherein the coating layer is adjacent to the nuclear particles.

28. The production method according to claim 26, wherein the drug is attached to the surface of at least one of the first nuclear-particle component and the second nuclear-particle component.

29. The production method according to claim 26, wherein the drug is an aniline derivative represented by the following formula (I-a):

[Formula 4]

(I-a)

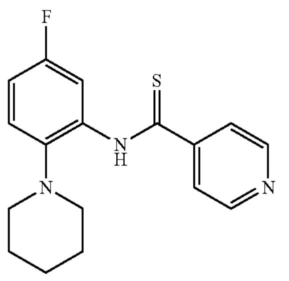

or a pharmaceutically acceptable salt thereof, or a hydrate thereof.

30. The production method according to claim 26, wherein the drug and the surfactant are retained in the many voids of the nuclear particles.

31. The production method according to claim 26, wherein an average aspect ratio of the first nuclear-particle component is 1.8 or more, and an average aspect ratio of the second nuclear-particle component is 1.0 to 1.7.

32. The production method according to claim 31, wherein the average aspect ratio of the first nuclear-particle component is 1.8 to 10.0.

33. The production method according to claim 31, wherein the average aspect ratio of the second nuclear-particle component is 1.0 to 1.5.

34. The production method according to claim 26, wherein a ratio of 50% particle size (D50) of the second nuclear-particle component based on volume distribution relative to the 50% particle size (D50) of the first nuclear-particle component based on volume distribution is 1:1.1 or less.

35. The production method according to claim 26, wherein the second nuclear-particle component is composed of at least two different components.

36. The production method according to claim 26, further comprising (e) obtaining a granular preparation by adding a pharmaceutically acceptable additive to the pharmaceutical preparation obtained in (d).

37. The production method according to claim 26, further comprising (e') obtaining a capsule-like preparation by enclosing the pharmaceutical preparation obtained in (d) with a film made of gelatin or a plant derived material.

38. A method for producing tablets, comprising tableting the pharmaceutical preparation according to claim 1.

39. A method for producing capsules, comprising encapsulating the pharmaceutical preparation according to claim 1.

40. A pharmaceutical preparation in the form of granules comprising nuclear particles and a coating layer coating the nuclear particles, wherein the nuclear particles comprise a drug, a first nuclear-particle component, a second nuclear-particle component and a nonionic surfactant, the drug is an aniline derivative represented by the following general formula (I):

[Formula 1]

(I)

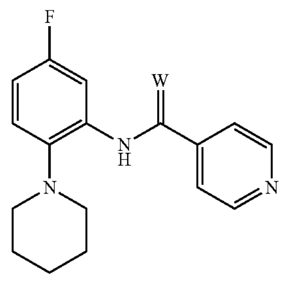

wherein W represents S or O, or a pharmaceutically acceptable salt thereof, or a hydrate thereof, the first nuclear-particle component is at least one crystalline cellulose having a shape selected from a needle-shape and a substantially columnar shape, and the second nuclear-particle component is at least one pharmaceutically acceptable additive having a substantially spherical shape, the nuclear particles are agglomerated particles formed from the first nuclear-particle component and the second nuclear-particle component, the nuclear particles have many voids formed between the first nuclear particle component and the second nuclear particle component, and a large amount of the drug and the surfactant are retained in the voids, wherein the surfactant is present as a liquid component, and at least one of the following conditions is satisfied: (i) a mass ratio of the first nuclear-particle component and the second nuclear-particle component is 1:1 to 1:10, (ii) an average aspect ratio of the first nuclear-particle component is 1.8 or more and an average aspect ratio of the second nuclear-particle component is 1.0 to 1.7, or (iii) the ratio of the needle-shape and/or a substantially columnar shape in the first nuclear particle component being 60 to 100%;

wherein the pharmaceutical preparation is made by a method comprising:

(a) mixing the first nuclear-particle component and the second nuclear-particle component to obtain a nuclear particle mixture, (b) dissolving or suspending the drug in a mixture of the nonionic surfactant and a solvent to obtain a mixed solution, (c) contacting the nuclear particle mixture obtained in (a) with the mixed solution obtained in (b) in a fluidized bed granulator to obtain the nuclear particles containing the first nuclear-particle component, the second nuclear-particle component, the drug and the surfactant, wherein voids are formed between the first nuclear-particle component and the second nuclear-particle component, and the drug and the nonionic surfactant are incorporated into and retained within the voids, the surfactant being present as a liquid component, and (d) coating the nuclear particles obtained in (c) to obtain the pharmaceutical preparation.

* * * * *